(12) United States Patent
Pastron

(10) Patent No.: US 8,998,806 B2
(45) Date of Patent: Apr. 7, 2015

(54) INSERTION AID FOR ORAL AND NASAL MEDICAL DEVICES

(75) Inventor: Nick Pastron, Long Island City, NY (US)

(73) Assignee: NJR Medical, Inc., Long Island City, NY (US)

(*) Notice: Subject to any disclaimer, the term of this patent is extended or adjusted under 35 U.S.C. 154(b) by 779 days.

(21) Appl. No.: 12/886,971

(22) Filed: Sep. 21, 2010

(65) Prior Publication Data

US 2011/0060192 A1  Mar. 10, 2011

Related U.S. Application Data

(63) Continuation-in-part of application No. 11/415,324, filed on May 1, 2006, now Pat. No. 7,827,985.

(51) Int. Cl.
| | | |
|---|---|---|
| A61B 1/32 | (2006.01) | |
| A61B 1/267 | (2006.01) | |
| A61M 25/01 | (2006.01) | |
| A61M 16/04 | (2006.01) | |
| A61J 15/00 | (2006.01) | |
| A61M 16/08 | (2006.01) | |

(52) U.S. Cl.
CPC ........... *A61M 25/01* (2013.01); *A61M 16/0463* (2013.01); *A61M 16/0488* (2013.01); *A61J 15/0026* (2013.01); *A61M 16/0495* (2014.02); *A61B 1/267* (2013.01); *A61M 16/0816* (2013.01); *A61M 2202/0413* (2013.01); *A61J 15/0003* (2013.01)

(58) Field of Classification Search
USPC ............. 128/200.26, 898; 600/187, 185, 188, 600/190, 193, 194, 199, 120–123, 128, 130, 600/138, 153, 156, 184, 201, 205, 240, 241, 600/226

See application file for complete search history.

(56) References Cited

U.S. PATENT DOCUMENTS

| | | | |
|---|---|---|---|
| 1,613,373 A | | 1/1927 | Beck |
| 2,127,215 A | | 8/1938 | Gwathmey |
| 2,756,742 A | * | 7/1956 | Barton .......................... 600/205 |
| 3,926,196 A | * | 12/1975 | Bornhorst et al. ....... 128/207.14 |
| 4,041,937 A | * | 8/1977 | Diaz ............................. 600/240 |
| 4,148,308 A | * | 4/1979 | Sayer ............................ 600/205 |
| 4,213,451 A | * | 7/1980 | Swenson ...................... 600/215 |

(Continued)

FOREIGN PATENT DOCUMENTS

WO  WO 2013002832  1/2013

OTHER PUBLICATIONS

International Search Report and Written Opinion in Related PCT Application No. PCT/US2011/067741, dated Oct. 22, 2012, 26 pages.

(Continued)

*Primary Examiner* — Rachel Young
(74) *Attorney, Agent, or Firm* — Kilpatrick Townsend & Stockton LLP

(57) ABSTRACT

Embodiments of the present invention include an insertion aid device with a handle, a tongue depressor, a tracheal suction catheter guide, and a guide with a recess formed by a pair of prongs. The guide may be configured to accommodate the cross-sectional shape of a tracheal suction catheter, a nasogastric tube, or an orogastric tube. The tracheal suction catheter guide may include a connection port configured to couple to an in-line suction catheter. A light source may be included with the insertion aid device.

4 Claims, 8 Drawing Sheets

(56) References Cited

U.S. PATENT DOCUMENTS

| | | | |
|---|---|---|---|
| 4,306,547 | A | 12/1981 | Lowell |
| 4,802,851 | A | 2/1989 | Rhoades |
| 4,883,426 | A | 11/1989 | Ferrer |
| 4,982,729 | A | 1/1991 | Wu |
| 5,025,806 | A | 6/1991 | Palmer et al. |
| 5,060,646 | A | 10/1991 | Page |
| 5,085,633 | A | 2/1992 | Hanifi et al. |
| 5,151,094 | A | 9/1992 | Hanifi |
| 5,215,522 | A | 6/1993 | Page et al. |
| 5,220,916 | A | 6/1993 | Russo |
| 5,378,226 | A | 1/1995 | Hanifi et al. |
| 5,394,865 | A | 3/1995 | Salerno |
| 5,694,922 | A | 12/1997 | Palmer |
| 5,845,634 | A * | 12/1998 | Parker ..................... 128/200.26 |
| 6,012,451 | A | 1/2000 | Palmer |
| 6,162,170 | A | 12/2000 | Foley et al. |
| 6,176,823 | B1 | 1/2001 | Foley et al. |
| 6,176,824 | B1 | 1/2001 | Davis |
| 6,238,213 | B1 | 5/2001 | Young et al. |
| 6,277,200 | B2 | 8/2001 | Xia et al. |
| 6,500,142 | B1 | 12/2002 | Harreld et al. |
| 6,843,769 | B1 * | 1/2005 | Gandarias ..................... 600/189 |
| 7,827,985 | B2 | 11/2010 | Pastron |
| 2004/0019256 | A1 | 1/2004 | Cubb et al. |
| 2005/0065411 | A1 | 3/2005 | Baldwin et al. |
| 2005/0090712 | A1 | 4/2005 | Cubb |
| 2005/0240081 | A1 | 10/2005 | Eliachar |
| 2006/0036133 | A1 | 2/2006 | Demsky |
| 2006/0065268 | A1 | 3/2006 | Koyama et al. |
| 2007/0093693 | A1 | 4/2007 | Geist et al. |
| 2007/0106122 | A1 | 5/2007 | Yokota |
| 2007/0272258 | A1 | 11/2007 | Pastron |
| 2011/0060192 | A1 | 3/2011 | Pastron |
| 2013/0006057 | A1 | 1/2013 | Pastron |

OTHER PUBLICATIONS

International Preliminary Report on Patentability in Related Application PCT/US2011/067741, dated Jan. 16, 2014, 12 pages.

Non-Final Office Action in related U.S. Appl. No. 13/171,151, dated May 30, 2013, 9 pages.

Response in related U.S. Appl. No. 13/171,151 dated Aug. 30, 2013, 15 pages.

Notice of Allowance in related U.S. Appl. No. 13/171,151 dated Dec. 24, 2013, 8 pages.

* cited by examiner

INSERTION AID FOR ORAL AND NASAL MEDICAL DEVICES

CROSS REFERENCE TO RELATED APPLICATIONS

This application is a continuation-in-part of U.S. patent application Ser. No. 11/415,324, filed on May 1, 2006, entitled INSERTION AID FOR ORAL AND NASAL MEDICAL DEVICES. The '324 application is hereby incorporated in its entirety by this reference.

FIELD OF THE INVENTION

The invention relates to a method and apparatus for maintaining the patient's mouth in an open position for oral cleaning and suctioning, orotracheal suctioning, and orogastric tube insertion, for uncoiling nasotracheal suctioning catheters and nasogastric tubes within the mouth during insertion, and for inserting orotracheal suctioning catheters.

BACKGROUND OF THE INVENTION

Oral cleaning instruments, oral suctioning instruments, and tracheal suctioning catheters are commonly used in health care patients with respiratory distress, critical illness, chronic illness, terminal illness, weakness, paralysis, or any patient requiring breathing support from a ventilator.

To perform oral cleaning, most caregivers use foam swabs with various antiseptic solutions to clean and moisten a patient's mouth. Oral suctioning is commonly performed by inserting a rigid plastic tube, often called a Yankauer suction, into a patient's mouth and throat to suction out saliva and mucus. The purpose of oral cleaning and oral suctioning is to remove bacteria that builds up in the mouth of patients who are unable to perform oral care, such as brushing their teeth. Various studies have shown that the buildup of bacteria in patients who are unable to perform oral care increases their risk of the nosocomial pneumonias, hospital acquired pneumonia ("HAP") and ventilator associated pneumonia ("VAP"), due to the aspiration of saliva and secretions with high levels of bacteria.

Tracheal suctioning is commonly performed to suction out secretions when a patient is too weak to cough up secretions on their own. Tracheal suctioning may be performed via either nasotracheal suctioning or orotracheal suctioning. In either case, a tracheal suction catheter is used, which typically is a soft, pliable plastic or rubber tube. In the case of nasotracheal suctioning, the tracheal suction catheter is inserted into the naris and continues down the trachea. Once the tracheal suction catheter reaches the trachea, the unwanted secretions are suctioned out. The nasotracheal suctioning method can cause trauma and bleeding to the nasal area. In addition, the suction catheter also has a tendency to coil in the back of the throat and may trigger the patient's gag reflex.

Typically, orotracheal suctioning is attempted in patients with increased coagulation times, nasal fractures, or deviated septums, or if coiling continues to occur in the nasotracheal approach. To perform orotracheal suctioning, the tracheal suction catheter is inserted into the mouth and continues down the trachea. Once the tracheal suction catheter reaches the trachea, the unwanted secretions are suctioned out. Similar to the nasotracheal suctioning method, the suction catheter has a tendency to coil in the back of the throat and may trigger the patient's gag reflex.

Patients are usually in an altered mental state from sedation, confusion, or being frightened and sometimes do not cooperate for oral cleaning, oral suctioning, and tracheal suctioning. Patients sometimes bite down on the cleaning and suctioning instruments, which can stop the oral cleaning, oral suctioning, and tracheal suctioning processes, and sometimes break a piece of the instrument off in the patient's mouth or even bite caregivers' fingers. Other problems that exist include instrument insertion trauma to the nose or mouth and the spread of bacteria from the mouth to the lungs during tracheal suctioning.

Nasogastric tubes and orogastric tubes are commonly used in the course of health-care, most frequently in the preparation before, during, and after surgery, for tube feedings, and in healthcare patients with stomach decompression or other stomach and bowel issues. Typically, these nasogastric/orogastric tubes are formed from resilient plastic material such as polyurethane, polyethylene, or silicone polymer. In addition, these tubes may be manufactured from surgical steel. The nasogastric and orogastric tubes typically have a proximal end, a distal end, and a central lumen or passageway. Further details about such tubes can be found in U.S. Pat. Nos. 4,778,448 and 4,634,425, the disclosures of which are incorporated herein by reference.

Nasogastric tubes and orogastric tubes are either inserted in the mouth or nose, down the throat, and into the stomach. The nasogastric and orogastric tubes have been a problem for patients and clinicians for some time. When a nasogastric tube is inserted into the patient's nose, sometimes the tube coils in the back of the throat and may trigger the patient's gag reflex. Similar to the problems experienced with the oral cleaning, oral suctioning, and tracheal suctioning, patients sometimes bite down on the orogastric tubes, which can stop the process, and sometimes break a piece of the tube off in the patient's mouth or even bite caregivers' fingers.

SUMMARY

Embodiments of the present invention include an insertion aid device with a handle comprising a distal end, a tongue depressor, a tracheal suction catheter guide, and a guide with a recess formed by a pair of prongs that extend from the distal end of the tongue depressor.

The tongue depressor includes a proximal end coupled to the distal end of the handle and a distal end, wherein the tongue depressor has a progressively smaller cross-sectional shape from the proximal end to the distal end. In some embodiments, the handle of the insertion aid device may be textured. In other embodiments, the handle length may be adjustable.

The tracheal suction catheter guide includes a first opening adjacent the proximal end of the tongue depressor, a second opening adjacent the distal end of the tongue depressor, and an enclosed channel connecting the first opening to the second opening. In some embodiments, the first opening may include a connection port configured to couple to an in-line suction catheter.

The guide is coupled to the distal end of the tongue depressor. In some embodiments, the recess is configured to accommodate the cross-sectional shape of a tracheal suction catheter, a nasogastric tube, or an orogastric tube.

A light source may be included with the insertion aid device, where the light source is located adjacent the tongue depressor.

BRIEF DESCRIPTION OF THE DRAWINGS

The invention may be understood by reference to the following description taken in conjunction with the accompanying drawings, in which, like reference numerals identify like elements, and in which.

DETAILED DESCRIPTION

Figure 1:
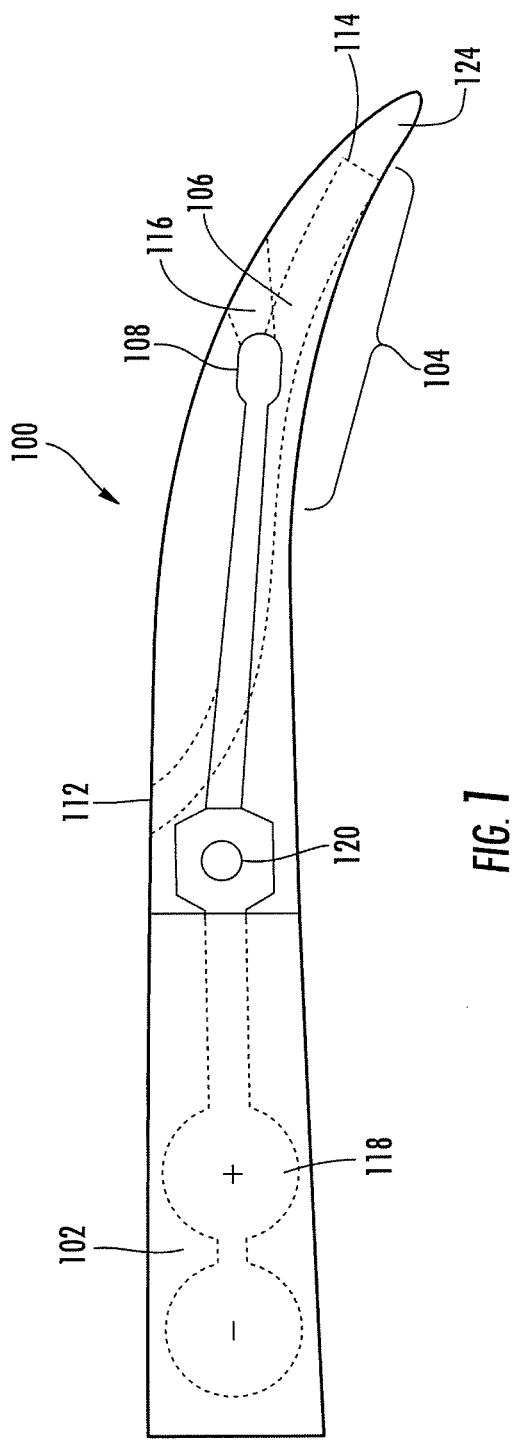
FIG. 1 is a cross-sectional view of an insertion aid device according to one embodiment of the present invention.

FIGS. 1-6 illustrate one embodiment of an insertion aid device 100. Alternative embodiments of the insertion aid device 100 are shown in FIGS. 7-8. The insertion aid device 100 comprises a handle 102, a tongue depressor 104, a tracheal suction catheter guide 106, a light source 108, and a guide 110.

In the embodiments illustrated in FIGS. 1-8, the handle 102 may be constructed of rigid material, such as plastic, steel, or any other suitable material. The handle 102 may have a circular cross-section or other suitable cross-sectional shape including but not limited to rectilinear, oval, crescent, triangular, pentagonal, hexagonal, octagonal, D-shaped, and I-shaped. However, one of skill in the relevant art will understand that the handle 102 may have any appropriate shape that allows a caregiver to use the insertion aid device 100 to accomplish the desired task without risk of injury to the patient or the caregiver. In some embodiments, the handle 102 may include a textured surface to prevent the insertion aid device 100 from slipping during use. In other embodiments, the handle 102 may include indentations for the caregiver's fingers when the handle is grasped.

The tongue depressor 104 is adjacent the handle 102, as illustrated in FIGS. 1-8. In some embodiments, the tongue depressor 104 is integrally formed with the handle 102. In other embodiments, the tongue depressor 104 is coupled to the handle 102 and may be formed of the same or different materials than the handle 102. For example, in some embodiments, the tongue depressor 104 may be constructed from rigid material such as plastic, steel, or any other suitable material, while the handle 102 is formed of similar or other materials. In other embodiments, the tongue depressor 104 is constructed of a flexible material such as rubber or soft plastic, while the handle 102 is formed of similar or other materials. In the embodiments shown in FIGS. 1-8, the tongue depressor 104 has a curved shape that approximately corresponds to the shape of the lower surface of a patient's mouth and tongue. The tongue depressor 104 is configured to contact a patient's mouth cavity without entering the patient's throat. In these embodiments, the tongue depressor 104 includes a declining surface along its length to aid in the depression of the tongue and to aid in the insertion of the insertion aid device 100. The tongue depressor 104 also has a progressively reducing cross-sectional shape, which becomes increasingly smaller in the direction of the distal end. However, one of skill in the relevant art will understand that the tongue depressor 104 may have any appropriate shape that allows a caregiver to use the insertion aid device 100 to accomplish the desired task without risk of injury to the patient or the caregiver.

As shown in FIGS. 1-2, 4, and 7-8, the tracheal suction catheter guide 106 is coupled to the tongue depressor 104 and positioned along the longitudinal axis of the insertion aid device 100. However, one of skill in the art will understand that any appropriate orientation of the tracheal suction catheter guide 106 may be used within the insertion aid device 100. For example, the tracheal suction catheter guide 106 may be positioned along an external surface of the tongue depressor 104. As shown in FIGS. 1-2, 4, and 7-8, the tracheal suction catheter guide 106 includes a first opening 112, which is located adjacent the proximal end of the tongue depressor 104. The tracheal suction catheter guide 106 includes a second opening 114 adjacent the distal end of the tongue depressor 104.

In an alternative embodiment shown in FIG. 7, the first opening 112 includes an angled projection 131 to facilitate insertion of the tracheal suction catheter 126 by allowing the caregiver to insert the tracheal suction catheter 126 at an angle that is less than 90 degrees from the central axis of the handle 102.

In another alternative embodiment shown in FIG. 8, the tracheal suction catheter guide 106 includes a connection port 132. The inner cross-sectional shape of the connection port 132 is configured to approximately conform to the cross-sectional shape of the first opening 112, while the outer cross-sectional shape of the connection port 132 is configured to engage with an in-line suction catheter 134. Typically, the in-line suction catheter 134 comprises a flexible, long tube 136 attached on a first end 138 to a suction valve 140. The suction valve 140 includes a suction port 142 that couples the in-line suction catheter 134 to a collection container and a device that generates suction (not shown). An opposing end 144 of the tube 136 is coupled to an elbow 146, where the elbow includes a breathing tube (endrotracheal or tracheotomy tube) port 148 and a ventilator port 150. Because the in-line suction catheter 134 is typically used with ventilated patients that are especially susceptible to infection, the tube 136 is enclosed in a sterile plastic sheath 152 to prevent the introduction of bacteria into the patient during suctioning. In the embodiment shown in FIG. 8, the suction port 142 of the in-line suction catheter 134 is coupled to the collection container and the device that generates suction (not shown). The breathing tube port 148 of the in-line suction catheter 134 is coupled to the connection port 132 of the insertion aid device 100, instead of a breathing tube. The ventilator port 150 that is typically connected to the ventilator remains uncoupled or capped when the in-line suction catheter 134 is used with the insertion aid device 100, as this port is not required for in-line suctioning with the insertion aid device 100. Likewise, an irrigation port 154, which typically is used to inject saline down the breathing tube to loosen secretions, is not required when using the in-line suction catheter 134 with the insertion aid device 100, but is required to irrigate and clean out debris from the in-line suction catheter 134 and the tracheal suction catheter guide 106. The suction valve 140 is used to control when suctioning is being administered through the in-line suction catheter 134. As a result, the insertion aid device 100 is configured to retrofit with the existing components of the in-line suction catheter 134.

In the embodiments illustrated in FIGS. 1-2 and 7-8, the light source 108 is coupled to the tongue depressor 104. An aperture 116 is formed in the tongue depressor 104 that allows light emitted from the light source 108 to pass through the tongue depressor 104. The light source 108 is coupled to a power source 118. In the embodiments shown in FIGS. 1-2 and 7-8, the power source 118 is positioned within the handle 102. However, one of skill in the relevant art will understand that the power source 118 may be positioned in any appropriate location either within or external to the insertion aid device 100. The power source 118 may include a battery or a power cord. In some embodiments, the handle 102 may include a rechargeable power source 118, where the handle 102 is placed on a battery charger between uses to re-charge the power source 118, and the tongue depressor 104 (which includes the tracheal suction catheter guide 106, the light source 108, and the guide 110) is removed from the handle 102 and disposed of after each use.

Figure 2:
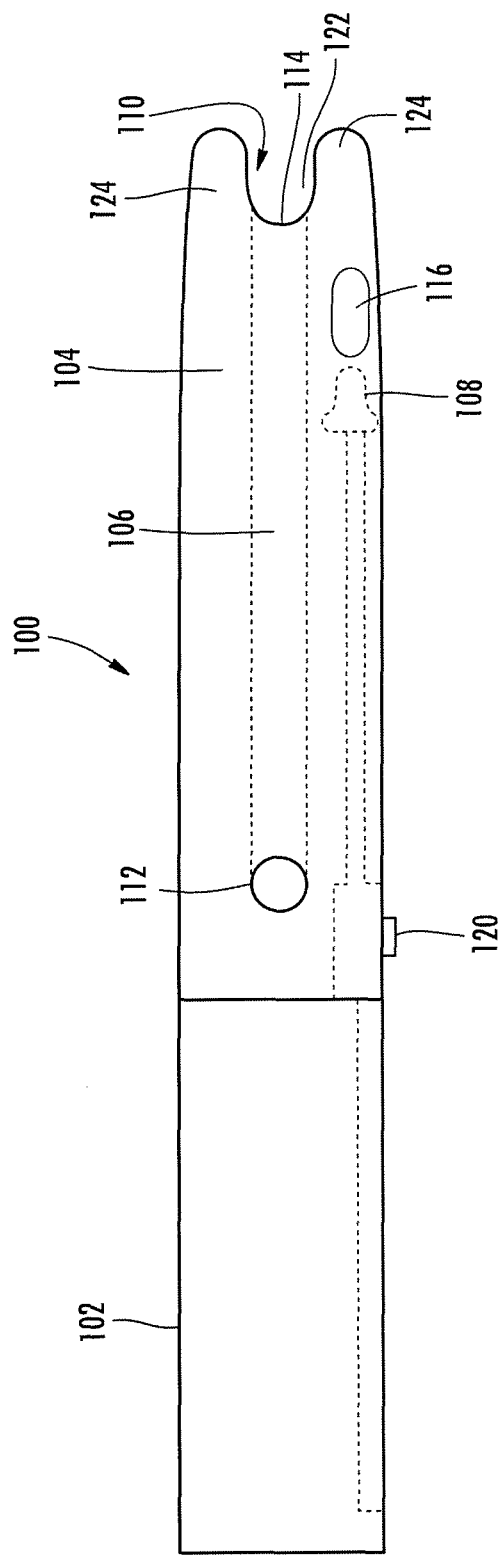
FIG. 2 is a top view of the insertion aid device of FIG. 1.

In the embodiment shown in FIGS. 1-2, a switch 120 is located near the proximal end of the tongue depressor 104. In the alternative embodiments shown in FIGS. 7-8, the switch 120 is positioned near the proximal end of the handle 102. In each of these embodiments, the operator of the insertion aid device 100 can activate the light source 108 by activating the switch 120. The light source 108 may be a conventional light bulb or a light emitting diode ("LED").

Figure 3:
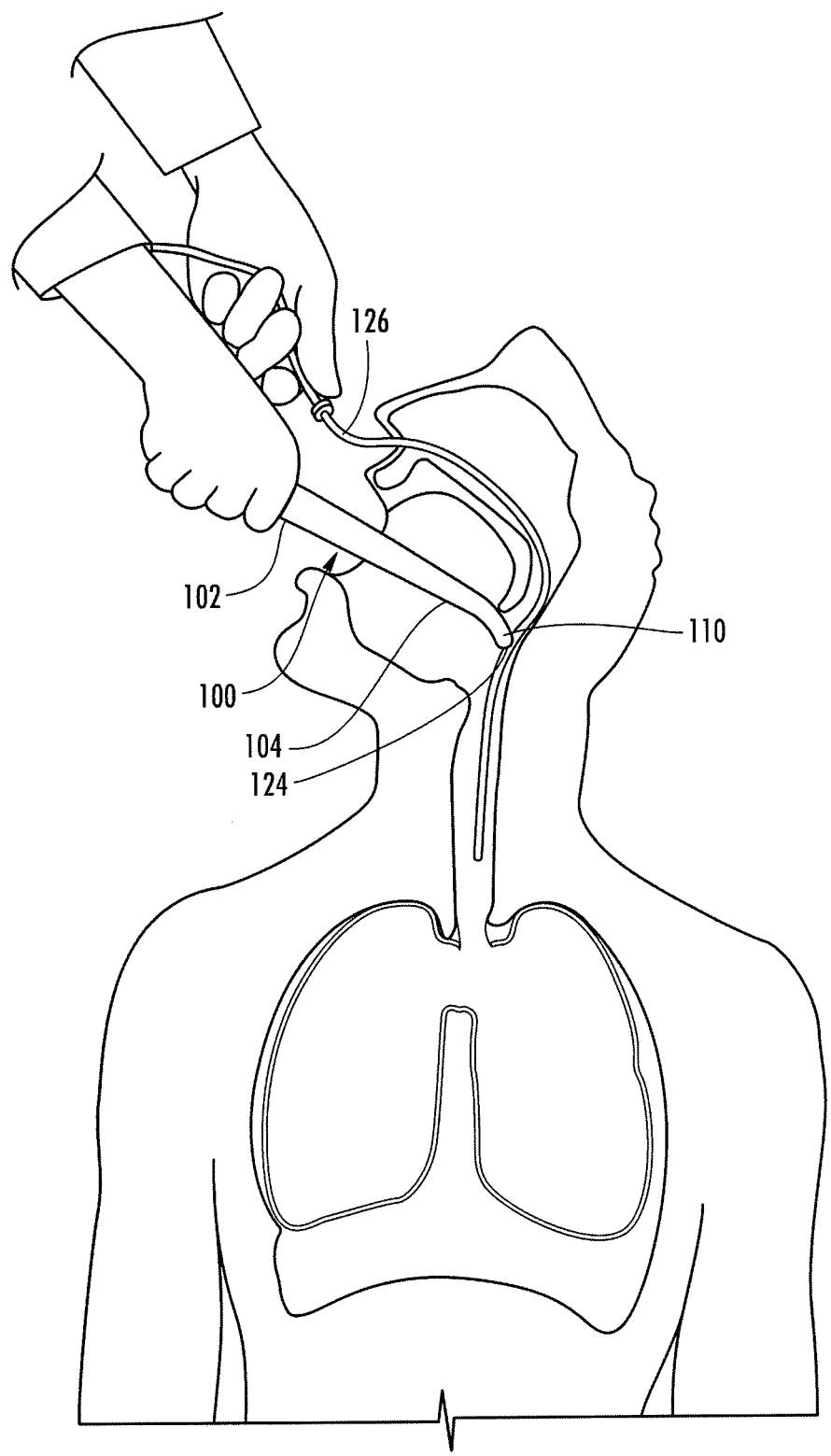
FIG. 3 is a cross-sectional view of the insertion aid device of FIG. 1 in use with an nasotracheal suctioning procedure.
Figure 4:
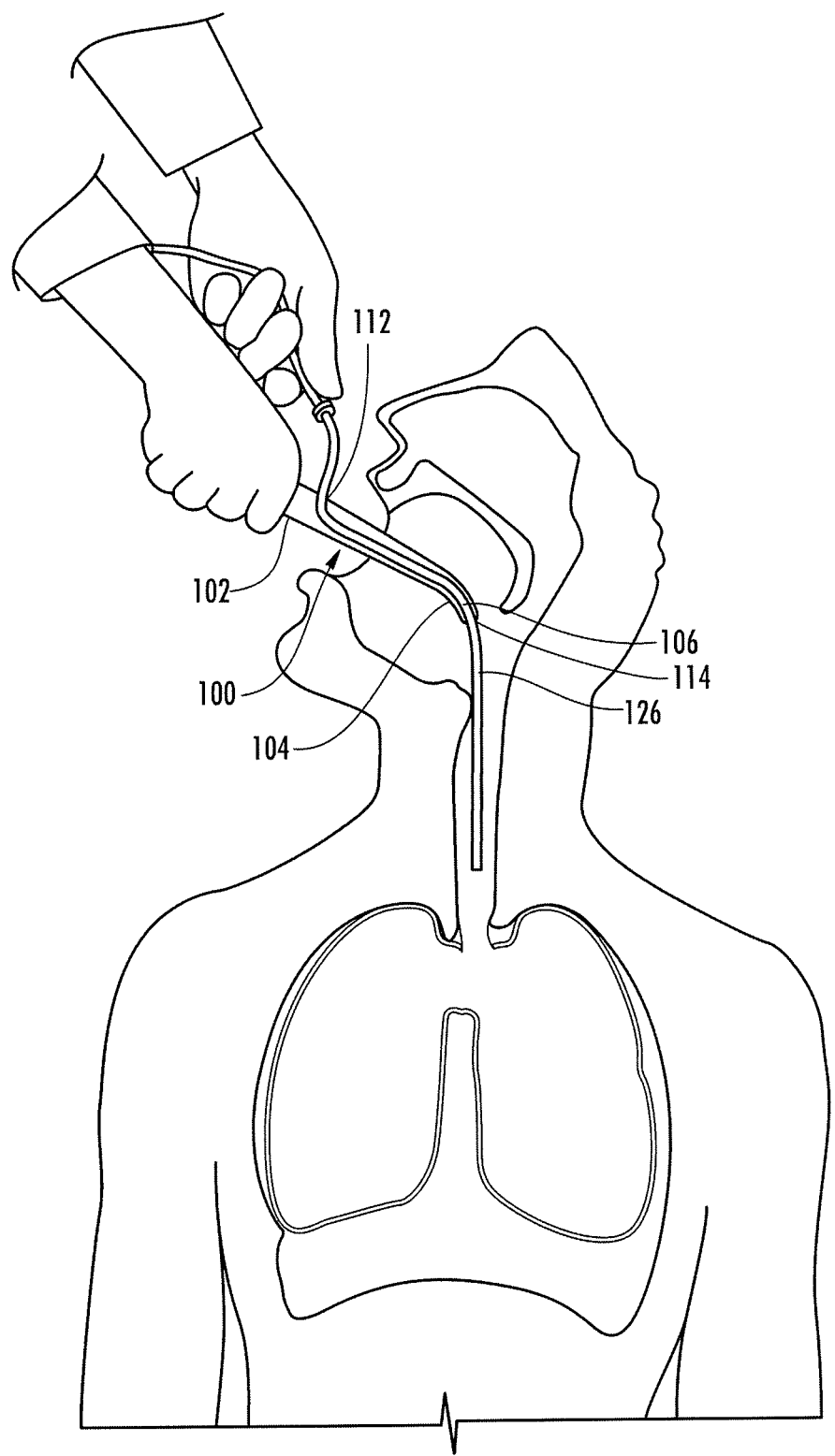
FIG. 4 is a cross-sectional view of the insertion aid device of FIG. 1 in use with an orotracheal suctioning procedure.
Figure 5:
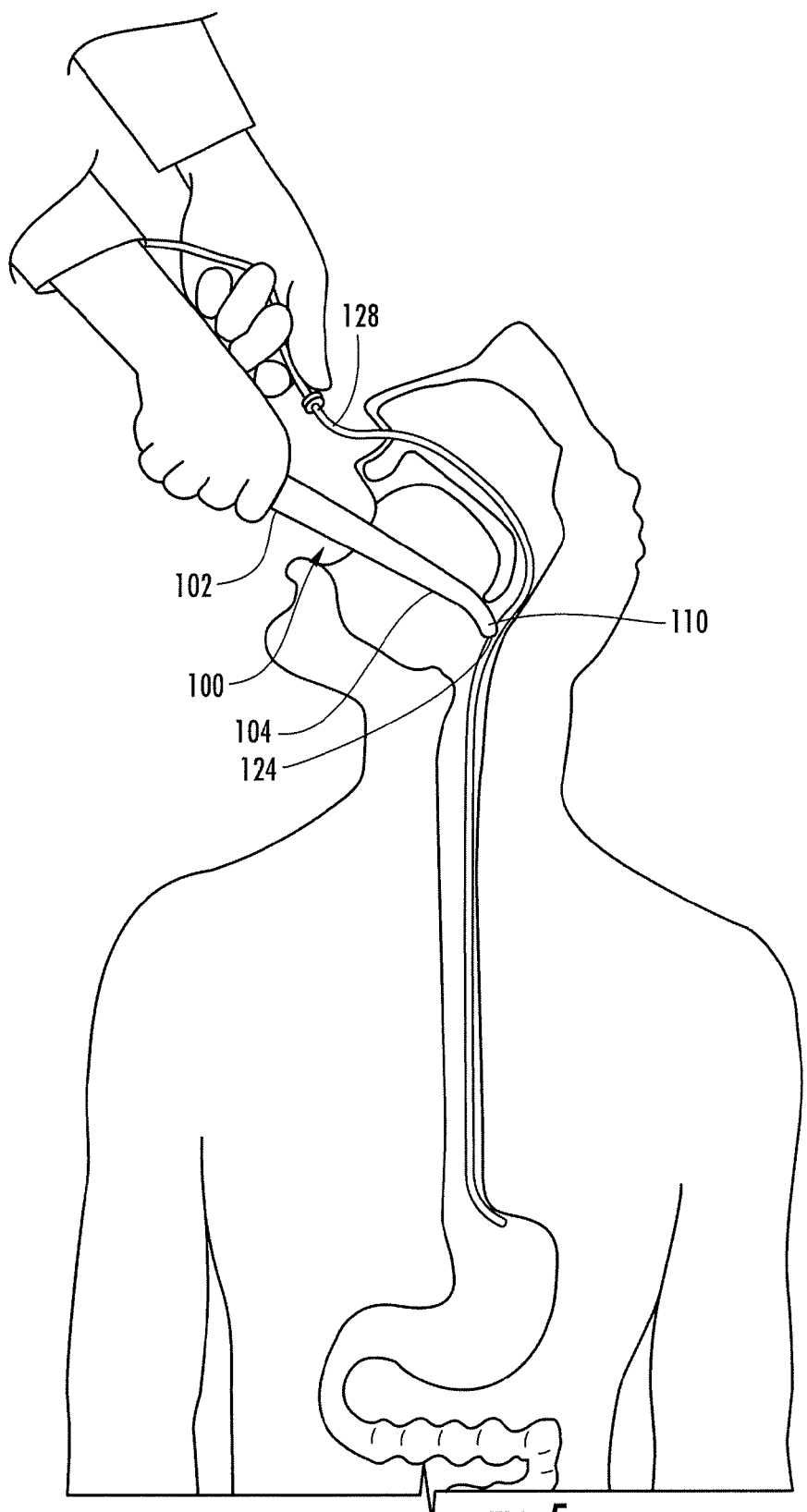
FIG. 5 is a cross-sectional view of the insertion aid device of FIG. 1 in use with a nasogastric tube insertion procedure.
Figure 6:
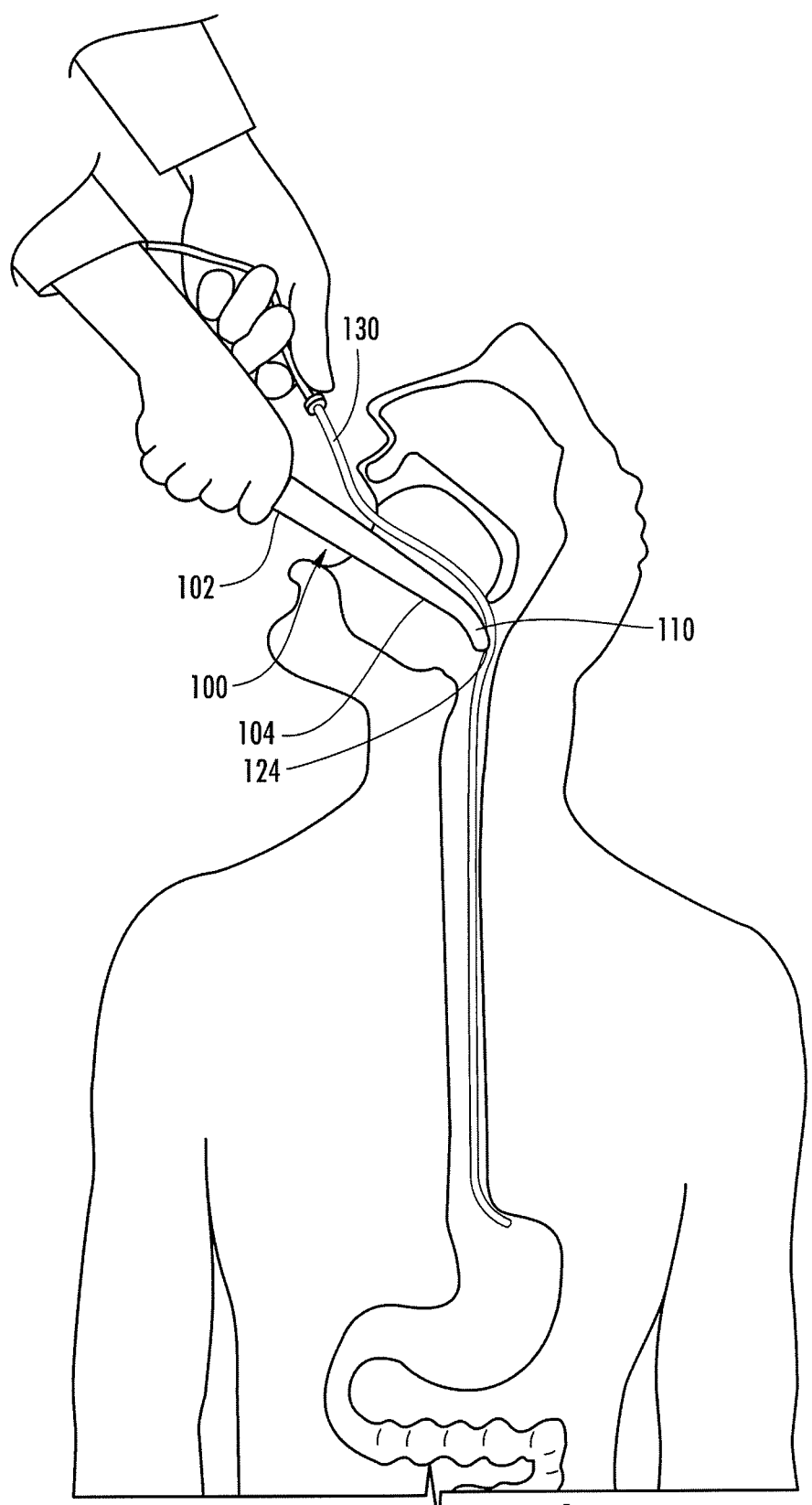
FIG. 6 is a cross-sectional view of the insertion aid device of FIG. 1 in use with an orogastric tube insertion procedure.
Figure 7:
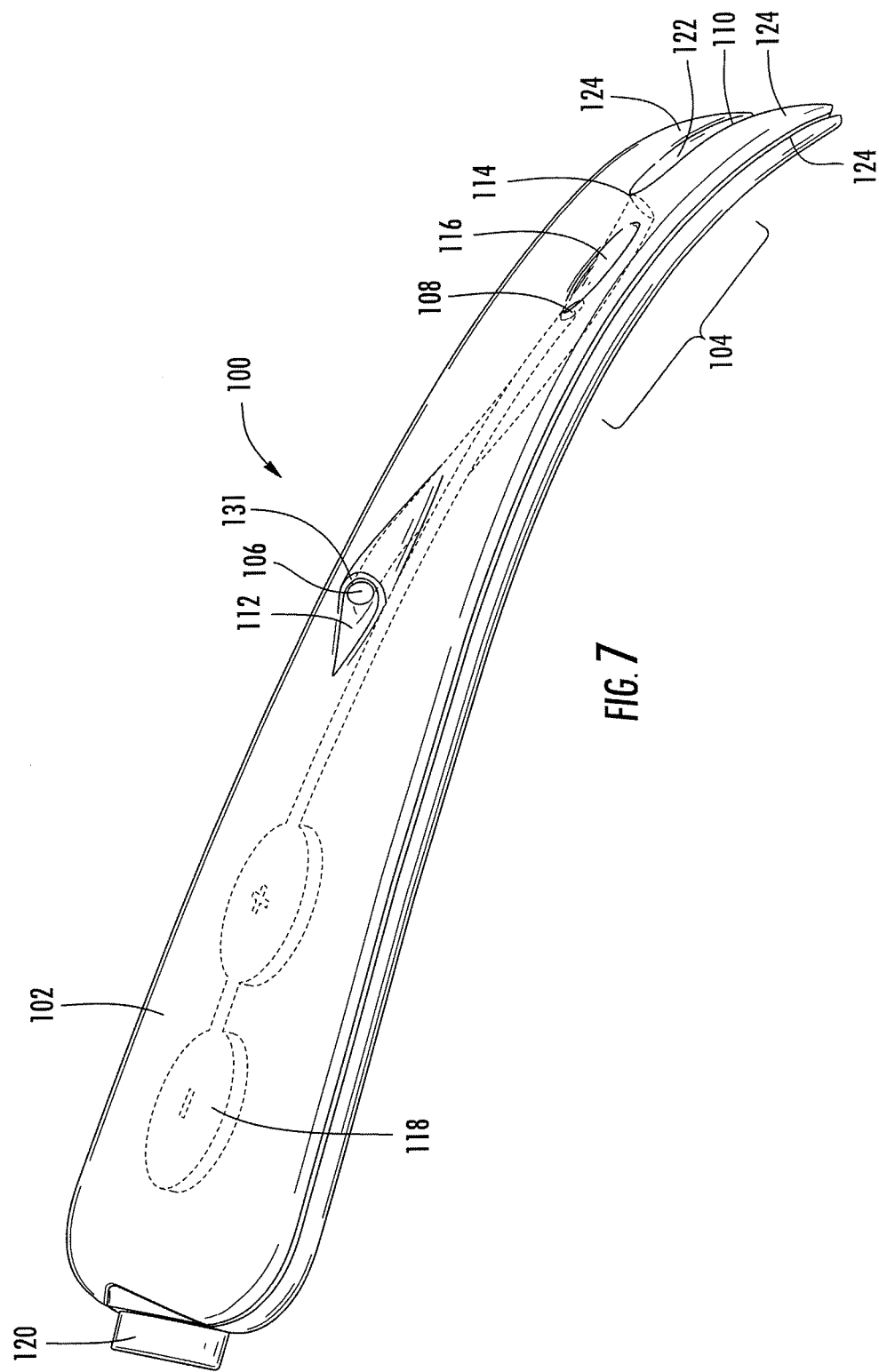
FIG. 7 is a perspective view of an insertion aid device according to an alternative embodiment of the present invention.
Figure 8:
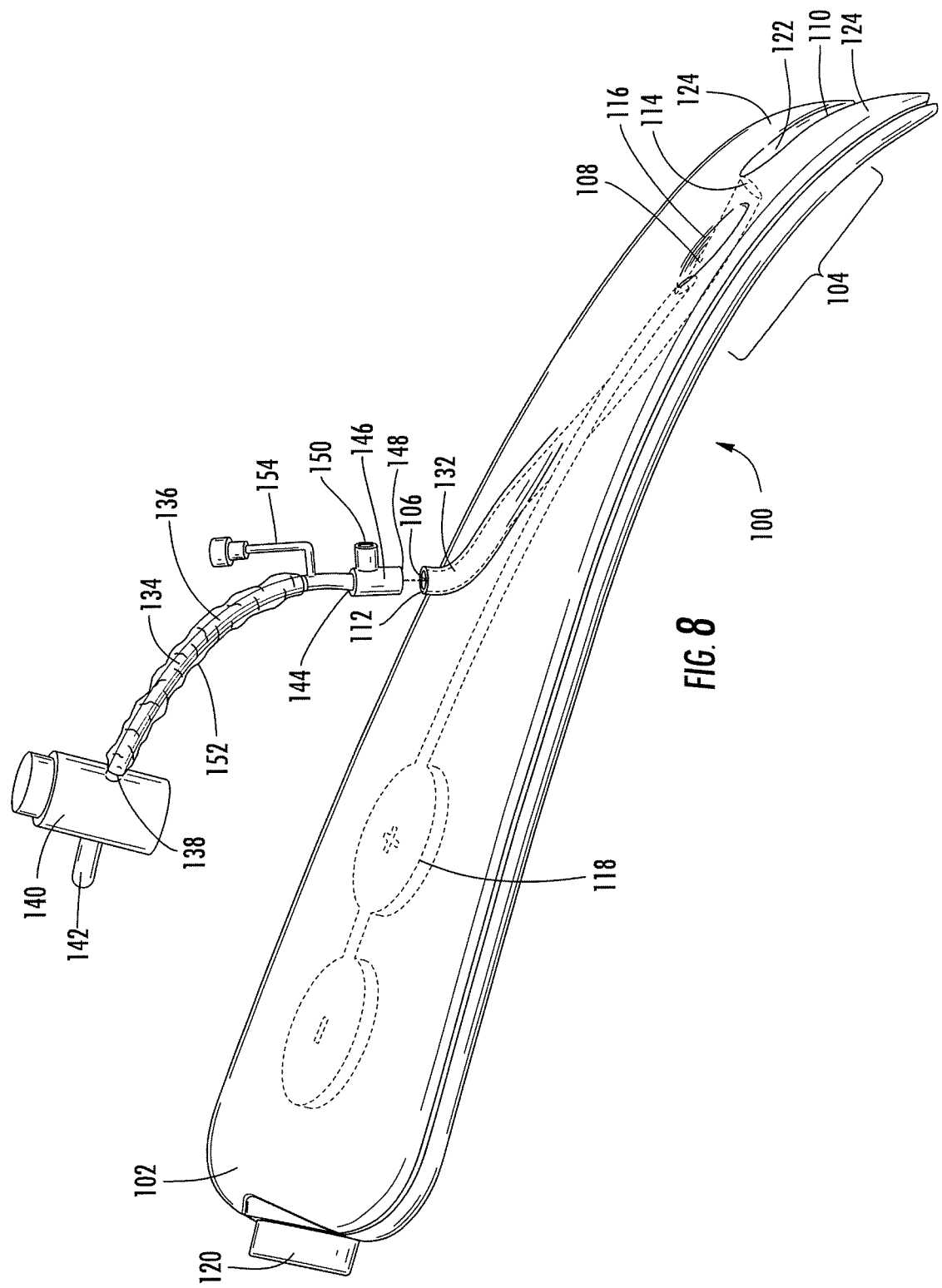
FIG. 8 is a perspective view of an insertion aid device according to another alternative embodiment of the present invention with an in-line suction catheter.

In the embodiments shown in FIGS. 1-8, the guide 110 is positioned at the distal end of the tongue depressor 104. In some embodiments, the guide 110 is integrally formed with the tongue depressor 104. In other embodiments, the guide 110 is coupled to the tongue depressor 104 and may be formed of the same or different materials than the tongue depressor 104. For example, in some embodiments, the guide 110 may be constructed from rigid material such as plastic, steel, or any other suitable material, while the tongue depressor 104 is formed of similar or other materials. In other embodiments, the guide 110 is constructed of a flexible material such as rubber or soft plastic, while the tongue depressor 104 is formed of similar or other materials. In yet other embodiments, the guide 110 is constructed from rigid material such as plastic, steel, or any other suitable material, which is then covered with soft rubber or a silicone overmold. As best illustrated in FIGS. 2, 7, and 8, the guide 110 has a recess 122 formed by two prongs 124 that extend along each side of the second opening 114. The recess 122 is shaped to accommodate the cross-sectional shape of a tracheal suction catheter 126 (as shown in FIGS. 3 and 4), a nasogastric tube 128 (as shown in FIG. 5), or an orogastric tube 130 (as shown in FIG. 6).

The length of the insertion aid device 100 may vary in accordance with the dimensions of the mouth of the patient. For example, the insertion aid device 100 may be used with a variety of patients ranging in age from infant to adult and having a range of sizes of mouth or oral cavities. Because the insertion aid device 100 may be used with a range of mouth or oral cavities, the insertion aid device 100 may be manufactured in a plurality of sizes, wherein each size is configured to fit a particular sized mouth or oral cavity. Typically, the insertion aid device 100 may be between approximately 6 inches long and 12 inches long and the circumference may be between approximately 1 inch and 3 inches. The length of the handle may be between approximately 3 inches and 4 inches. However, one of skill in the relevant art will understand that any suitable length may be used that will accomplish the desired task without risk of injury to the patient or the caregiver. In some alternative embodiments (not shown), the insertion aid device 100 may include a telescoping design that allows the length of the insertion aid device 100 to be adjusted as needed.

In use, the insertion aid device 100 performs several functions. Specifically, the insertion aid device 100 is designed to improve oral suctioning and cleaning, nasal and oral tracheal suctioning, and insertion of nasal and oral gastric tubes and feeding tubes. The steps involved in each of these procedures is discussed in detail as follows.

When performing oral suctioning and cleaning, nasotracheal suctioning, orotracheal suctioning, and orogastric tube insertion, a caregiver begins each process by inserting the insertion aid device 100 into the patient's mouth. The tongue depressor 104 is placed in contact with the lower portion of the patient's mouth and tongue. The shape of the tongue depressor 104 depresses the tongue and maintains the patient's mouth in an open position, preventing the patient from fighting the caregiver and providing improved viewing of the oral cavity. Once the insertion aid device 100 has been inserted, the caregiver may turn on the light source 108 for further improvement in oral cavity viewing. With the patient's mouth now held in an open position by the insertion aid device 100, the caregiver may proceed to perform the specific steps associated with each of these processes.

For example, the caregiver proceeds to perform oral cleaning with a foam swab and various antiseptic solutions and/or oral suctioning without risk of the patient biting down on the swab or suctioning device.

To perform nasotracheal suctioning, as shown in FIG. 3, the caregiver inserts the tracheal suction catheter 126 into the patient's narias. Once the tube is visible in the back of the mouth, the caregiver then engages the guide 110 with the tracheal suction catheter 126 to position the tracheal suction catheter 126 into the trachea until the desired depth of the trachea is reached to suction unwanted secretions out. The guide 110 prevents the tracheal suction catheter 126 from coiling in the back of the throat and decreases the chances of triggering the patient's gag reflex.

To perform orotracheal suctioning, as shown in FIG. 4, the caregiver inserts the tracheal suction catheter 126 into the tracheal suction catheter guide 106 until the desired depth of the trachea is reached to suction unwanted secretions out. The tongue depressor 104 prevents the patient from biting down on the tracheal suction catheter 126. The tracheal suction catheter guide 106 prevents the tracheal suction catheter 126 from coiling in the back of the throat and decreases the chances of triggering the patient's gag reflex. Furthermore, the tracheal suction catheter guide 106 prevents the introduction of bacteria into the oral cavity and consequently prevents the introduction of bacteria into the lungs, decreasing the risk of infection.

To perform orogastric tube insertion, as shown in FIG. 6, the caregiver inserts the orogastric tube 130 into the patient's mouth. Once the tube reaches the back of the patient's mouth, the caregiver then engages the guide 110 with the orogastric tube 130 to position the orogastric tube 130 down the throat and into the stomach. The tongue depressor 104 prevents the patient from biting down on the orogastric tube 130. The guide 110 prevents the orogastric tube 130 from coiling in the back of the throat and decreases the chances of triggering the patient's gag reflex.

To perform nasogastric tube insertion, the caregiver begins by inserting the nasogastric tube 128 into the patient's narias and down into the throat. In the event the nasogastric tube 128 coils in the back of the patient's mouth, the caregiver inserts the insertion aid device 100 into the patient's mouth as described above. Once the insertion aid device 100 has been inserted, the caregiver may turn on the light source 108 for further improvement in oral cavity viewing. With the patient's mouth now held in an open position by the insertion aid device 100, the caregiver retracts the nasogastric tube 128 until the caregiver can see the tip of the nasogastric tube 128 in the back of the patient's mouth. As shown in FIG. 5, once the tube is visible in the back of the patient's mouth, the caregiver then engages the guide 110 with the nasogastric tube 128 to position the nasogastric tube 128 down the throat and into the stomach. The guide 110 prevents the nasogastric tube 128 from coiling in the back of the throat and decreases the chances of triggering the patient's gag reflex.

The foregoing is provided for purposes of illustrating, explaining, and describing embodiments of the present invention. Further modifications and adaptations to these embodiments will be apparent to those skilled in the art. The features and aspects of the present invention have been described or depicted by way of example only and are therefore not intended to be interpreted as required or essential elements of the invention unless otherwise so stated. It should be understood, therefore, that the foregoing relates only to certain exemplary embodiments of the invention, and that numerous changes and additions may be made thereto without departing from the spirit and scope of the invention as defined by any appended claims.

That which is claimed is:

1. A method of using an insertion aid device, the method comprising:
    (a) providing an insertion aid device that comprises
        (i) a handle comprising a distal end,
        (ii) a tongue depressor comprising a proximal end adjacent the distal end of the handle and a distal end,
        (iii) a tracheal suction catheter guide comprising a first opening adjacent the proximal end of the tongue depressor, a second opening adjacent the distal end of the tongue depressor, and an enclosed channel connecting the first opening to the second opening; and
        (iv) a guide adjacent the distal end of the tongue depressor, wherein the guide comprises a recess formed by a pair of prongs that extend from the distal end of the tongue depressor adjacent the second opening, wherein each tong comprises a longitudinal axis that substantially aligns with the radius of curvature of the tongue depressor;
    (b) inserting the insertion aid device into a patient's mouth until the distal end of the tongue depressor is placed in contact with the lower portion of the patient's mouth in a location where the tongue depressor extends substantially along an entire length of the patient's tongue without entering the patient's throat;
    (c) inserting a tracheal suction catheter into the patient's narias until the tracheal suction catheter is visible in the back of the patient's mouth; and
    (d) engaging the guide with the tracheal suction catheter by positioning the tracheal suction catheter between the pair of prongs.

2. The method of claim 1, further comprising the step of inserting a foam swab with antiseptic solution into the patient's mouth.

3. The method of claim 1, wherein the guide positions the tracheal suction catheter into the trachea until the tracheal suction catheter reaches the desired depth of the trachea.

4. The method of claim 1, further comprising the step of providing a light source coupled to the insertion aid device.

* * * * *